US008713988B2

(12) United States Patent  (10) Patent No.: US 8,713,988 B2
Biesak  (45) Date of Patent: May 6, 2014

(54) USE OF GAS VOID FRACTION MEASUREMENT IS THE CLOSED LOOP CONTROL OF A FERMENTATION PROCESS

(75) Inventor: John Biesak, Durham, CT (US)

(73) Assignee: CiDRA Corporate Services Inc., Wallingford, CT (US)

( * ) Notice: Subject to any disclaimer, the term of this patent is extended or adjusted under 35 U.S.C. 154(b) by 337 days.

(21) Appl. No.: 13/148,715

(22) PCT Filed: Feb. 16, 2010

(86) PCT No.: PCT/US2010/024255
§ 371 (c)(1),
(2), (4) Date: Nov. 21, 2011

(87) PCT Pub. No.: WO2010/094018
PCT Pub. Date: Aug. 19, 2010

(65) Prior Publication Data
US 2012/0064507 A1  Mar. 15, 2012

Related U.S. Application Data

(60) Provisional application No. 61/152,387, filed on Feb. 13, 2009.

(51) Int. Cl.
*G01N 29/024* (2006.01)
(52) U.S. Cl.
USPC ............. 73/19.1; 73/19.01; 73/19.03; 73/149
(58) Field of Classification Search
USPC .................. 73/19.01, 19.03, 19.1, 19.11, 149
See application file for complete search history.

(56) References Cited

U.S. PATENT DOCUMENTS

| | | | | |
|---|---|---|---|---|
| 2,883,344 A | * | 4/1959 | McKinney | 516/115 |
| 4,084,426 A | * | 4/1978 | Gales | 73/60.11 |
| 4,677,304 A | * | 6/1987 | Camp et al. | 250/577 |
| 5,035,139 A | * | 7/1991 | Hoefelmayr et al. | 73/223 |
| 5,266,033 A | * | 11/1993 | Rogers et al. | 434/226 |
| 5,454,255 A | * | 10/1995 | Kraus et al. | 73/19.03 |
| 5,597,950 A | * | 1/1997 | Mullen | 73/60.11 |
| 5,635,637 A | * | 6/1997 | Boult et al. | 73/223 |
| 5,660,977 A | | 8/1997 | Flores-Cotera et al. | |
| 6,439,035 B1 | * | 8/2002 | Yasui et al. | 73/60.11 |
| 7,134,320 B2 | | 11/2006 | Gysling et al. | |
| 7,165,464 B2 | | 1/2007 | Gysling et al. | |
| 7,343,820 B2 | | 3/2008 | Gysling et al. | |
| 7,363,800 B2 | | 4/2008 | Gysling | |
| 7,367,240 B2 | | 5/2008 | Gysling et al. | |
| 8,490,464 B1 | * | 7/2013 | Selby | 73/19.1 |

(Continued)

OTHER PUBLICATIONS

International Search Report issued on Jul. 8, 2010 in corresponding international application No. PCT/US10/24255 (3 pages).

*Primary Examiner* — David A Rogers

(57) ABSTRACT

A technique related to a fermentation process; where a signal processor receives a signal containing information about an amount of entrained air in a mixture forming part of a fermentation process in a tank; and determines a level of foam in the tank based at least partly on the amount of entrained air in the mixture. The signal processor may also provide a control signal for controlling an amount of defoamer (or antiforming agent) added to the mixture in the tank so as to control the production of foam within the tank by controlling the amount of defoamer added to the mixture in the tank.

46 Claims, 5 Drawing Sheets

(56) References Cited

U.S. PATENT DOCUMENTS

| | | |
|---|---|---|
| 2004/0031335 A1 | 2/2004 | Fromme et al. |
| 2007/0044572 A1 | 3/2007 | Davis et al. |
| 2007/0131033 A1* | 6/2007 | Stencel ............................ 73/587 |
| 2008/0141756 A1 | 6/2008 | Gysling et al. |
| 2008/0175951 A1 | 7/2008 | Rule |

* cited by examiner

Apparatus (e.g. a system 10)

Entrained air measurement device 12 configured to measure an amount of entrained air in a mixture forming part of a fermentation process in a tank and to provide a signal containing information about the amount of entrained air in the mixture.

—13

Signal processor 14 having one or more modules 16 configured to receive the signal containing information about the amount of entrained air in the mixture forming part of the fermentation process in the tank, and determine a level of foam in the tank based at least partly on the amount of entrained air in the mixture.

*FIG. 1*

A signal processor 14

One or more modules 16 configured
to receive the signal containing information
about the amount of entrained air in the mixture
forming part of the fermentation process in the tank,
and determine a level of foam in the tank based at
least partly on the amount of entrained
air in the mixture.

*FIG. 5*

USE OF GAS VOID FRACTION MEASUREMENT IS THE CLOSED LOOP CONTROL OF A FERMENTATION PROCESS

CROSS-REFERENCE TO RELATED APPLICATIONS

This application corresponds to international patent application serial no. PCT/US2010/024255, filed 16 Feb. 2010, which claims benefit to provisional patent application Ser. No. 61/152,387 (WFVA/CCS nos. 712-2.316//0012P), filed 13 Feb. 2009, which is incorporated by reference in their entirety.

BACKGROUND OF THE INVENTION

1. Field of Invention

This invention relates to a fermentation process; more particularly, this invention relates to a technique for determining a level of foam in the tank based at least partly on an amount of entrained air in a mixture forming part of a fermentation process in a tank, as well as for controlling an amount of defoamer added to the mixture in the tank so as to control the production of foam within the tank.

2. Description of Related Art

There are a number of known processes that use fermentation to create end products in the food and feed industry. For example, the manufacture of L-Lysine (an amino acid essential for human and animal nutrition) can be done through a fermentation process. Ethanol is also an example of a product that is produced through a fermentation process. Depending on the specific fermentation process and results, the process may be continuous (continuous feed and effluent) or the process may be a batch process.

The fermentation process typically involves the introduction of feed stock and nutrients into the batch or continuous process within a fermentation tank or vessel. The process may be open to atmosphere or performed under a controlled pressure in a closed tank.

Additionally, the process may involve the introduction of oxygen, $CO^2$ and other gases, and can include an agitator or other device to circulate the mixture within the fermentation tank.

In certain known fermentation processes, such as the manufacture of L-Lysine, it may be desirable to control the amount foam produced at the top of the fermentation tank due to the fermentation process. Different methods may be used to control the amount of foam at the top of the mixture, including the introduction of surfactants and other defoamer chemicals to the mixture, mechanical removal devices, and controlling the feed stock, nutrients and gas infusion.

Foam at the top of a fermentation tank may be detected through the use of several known methods, including the placement of a foam sensor or level probe within the fermentation tank. The amount of defoamer may be adjusted to control the indication of foam at the sensor. However, this known process is not very accurate, and significant excess defoamer is added to ensure that foam is not indicated in the process, resulting in a waste of such defoamers and added wasteful cost related to the same.

In view of the aforementioned, there is a need in industry applications to be able to detect foam at the top of a fermentation tank, and to reduce the amount of defoamer that is added to ensure that foam is not indicated in the process.

SUMMARY OF THE INVENTION

The present invention provides a new method and apparatus for determining a level of foam in the tank based at least partly on an amount of entrained air in a mixture forming part of a fermentation process in a tank.

The method may include receiving a signal containing information about an amount of entrained air in a mixture forming part of a fermentation process in a tank; and determining a level of foam in the tank based at least partly on the amount of entrained air in the mixture.

The level of foam in the tank may be determined based at least partly on the amount of foam produced in the tank being directly related to the magnitude of the entrain air detected in the mixture.

The method may comprise measuring a sample of the mixture either as an effluent or discharge provided from the tank via a discharge port, or as a representative sample provided from the tank via a by-pass loop, or by measuring the sample of the mixture directly in the tank.

The method may comprise arranging an entrained air measurement device configured to measure the amount of entrained air in the mixture and to provide the signal based at least partly on the measurement of the amount of entrained air in the mixture, including where the information contained in the signal is based at least partly on the speed of sound propagating through the mixture. The entrained air measurement device may be arranged in relation to the discharge port configured to measure the amount of entrained air in the effluent or discharge from the tank and to provide the signal based at least partly on the measurement of the amount of entrained air in the effluent or discharge from the tank. Alternatively, the entrained air measurement device may be arranged in relation to the by-pass loop configured to measure the amount of entrained air in the representative sample of the mixture within the tank and to provide the signal based at least partly on the measurement of the amount of entrained air in the representative sample of the mixture, including a by-pass loop set-up is arranged on the side of the tank to circulate the mixture through a pipe having the entrained air measurement device arranged thereon. Alternatively, the entrained air measurement device may be arranged within the tank configured to measure the amount of entrained air in the mixture within the tank and to provide the signal based at least partly on the measurement of the amount of entrained air in the mixture within the tank. The entrained air measurement device may take the form of a SONAR-based measurement device.

The method may comprise providing a control signal for controlling an amount of defoamer added to the mixture in the tank so as to control the production of foam within the tank by controlling the amount of defoamer added to the mixture in the tank.

The method may comprise fermenting lysine in a fermentation process.

The method may comprise providing either a stock feed, a nutrient feed, or some combination thereof, including where the nutrient feed is provided as a continuous flow during the fermentation process.

The method may comprise arranging an antifoam device configured to provide an amount of defoamer added to the mixture in the tank so as to control the production of foam within the tank; agitating the mixture in the tank, including using an agitator arranged within the tank; or providing air to the mixture in the tank, including using an air sparger arranged within the tank; or a combination thereof; using a closed loop control configured to provide a foamer addition based at least partly upon a measurement of entrained gas; or some combination thereof.

The method may also be implemented using one or more of the features set forth above in relation to the processor or system.

Signal Processor

According to some embodiments, the present invention may be implemented in apparatus taking the form of a processor, a signal processor, or a signal processor module comprising one or more modules configured to: receive a signal containing information about an amount of entrained air in a mixture forming part of a fermentation process in a tank; and determine a level of foam in the tank based at least partly on the amount of entrained air in the mixture. The signal processor may also include one or more of the features set forth above, including providing a control signal for controlling an amount of defoamer (or antiforming agent) added to the mixture in the tank so as to control the production of foam within the tank by controlling the amount of defoamer added to the mixture in the tank. The scope of the invention is intended to include the signal processor being a stand alone component or module, as well as the signal processor forming part a combined SONAR-based meter and signal processing device.

System

According to some embodiments, the present invention may be implemented in apparatus taking the form of a system comprising an entrained air measurement device in combination with a signal processor. The entrained air measurement device configured to measure the amount of entrained air in a mixture forming part of a fermentation process in a tank and to provide a signal containing information about the amount of entrained air in the mixture. The signal processor may have one or more modules configured to receive the signal containing information about the amount of entrained air in a mixture forming part of the fermentation process in the tank, and determine a level of foam in the tank based at least partly on the amount of entrained air in the mixture. The system may also include one or more of the features set forth above.

Computer-Readable Storage Medium

According to some embodiments, the present invention may be implemented in apparatus taking the form of a computer-readable storage medium having computer-executable components for performing the steps of the aforementioned method.

BRIEF DESCRIPTION OF THE DRAWING

The drawing includes FIGS. 1-5, which are not drawn to scale, as follows:

FIG. 1 is a block diagram showing a system, apparatus or device according to some embodiment of the present invention.

FIG. 5 is a block diagram showing a signal processor according to some embodiment of the present invention.

DETAILED DESCRIPTION OF BEST MODE OF THE INVENTION

FIG. 1

The Basic Invention

FIG. 1 shows apparatus taking the form of a system generally indicated as 10 according to some embodiments of the present invention, that comprises an entrained air measurement device 12 in combination with a signal processor 14.

The entrained air measurement device 12 may be configured as a data gathering device to measure the amount of entrained air in a mixture forming part of a fermentation process in a tank 20 and to provide a signal, e.g. along line 13, containing information about the amount of entrained air in the mixture.

The signal processor 14 may have one or more modules configured to receive the signal containing information about the amount of entrained air in the mixture forming part of a fermentation process in the tank, and determine a level of foam in the tank based at least partly on the amount of entrained air in the mixture. The signal processor 14 may also be referred to herein as a processor or a signal processor module for providing the signal processing technology for implementing the present invention.

Figure 2:
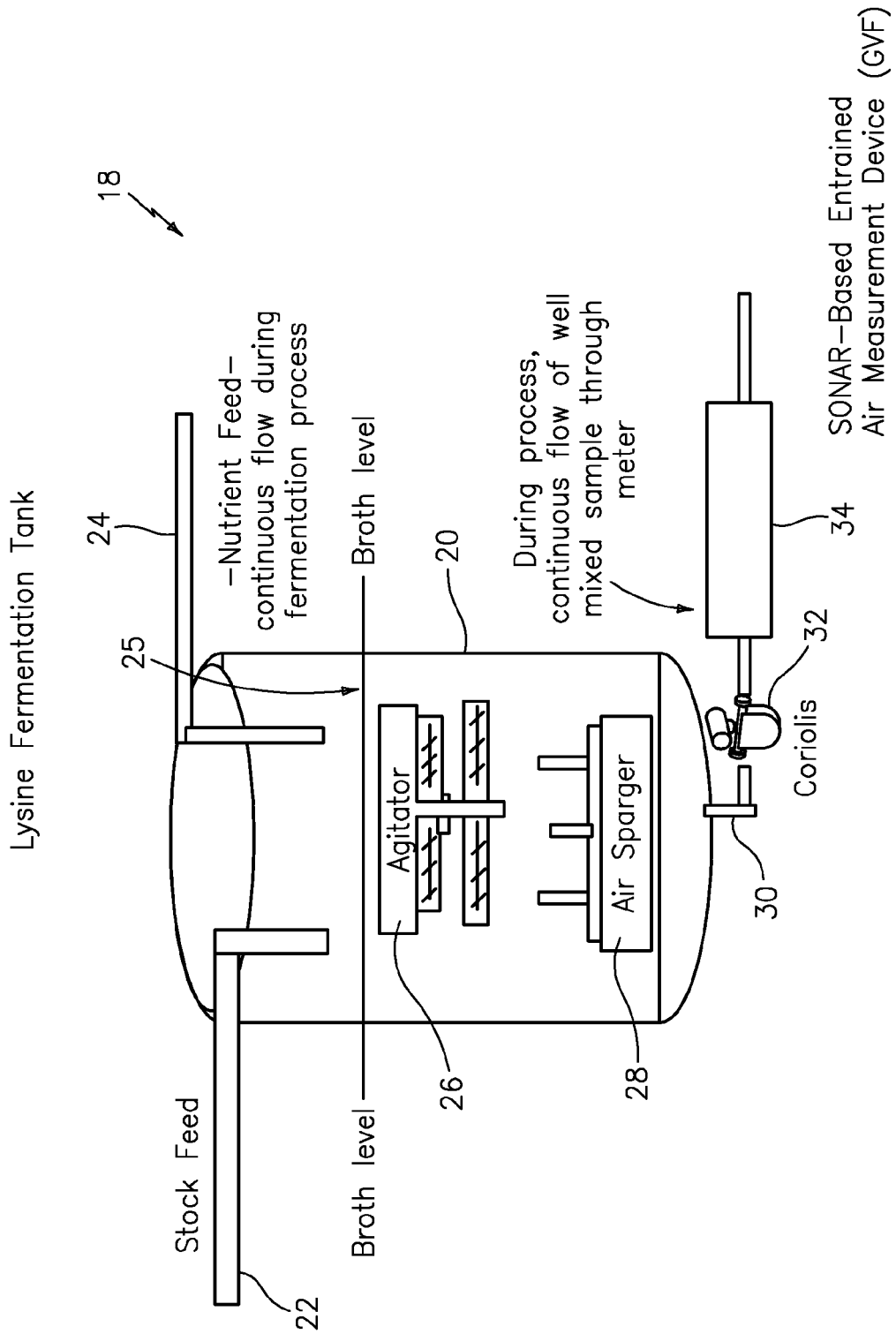
FIG. 2 is a diagram showing a possible implementation for a lysine fermentation tank according to some embodiment of the present invention.
Figure 4:
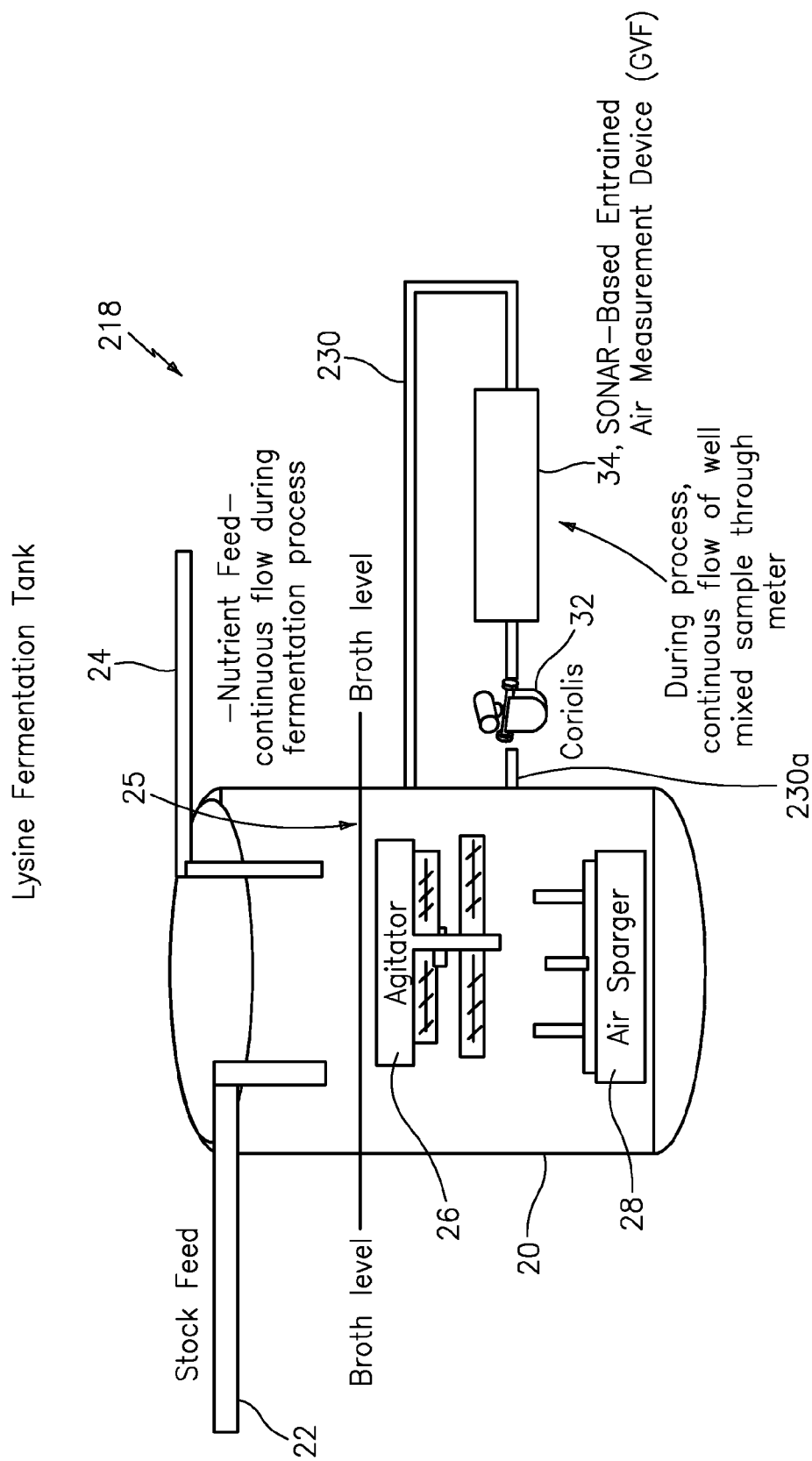
FIG. 4 is a diagram showing an alternative implementation for a lysine fermentation tank according to some embodiment of the present invention.

FIGS. 2 and 4

The Lysine Fermentation Tank

FIG. 2 shows a lysine fermentation process generally indicated as 18 for processing a mixture in a fermentation tank 20 according to some embodiments of the present invention. In the process, a stock feed is provide from a pipe 22 into the tank 20, and a nutrient feed is provided from a pipe 24 into the tank 20, so as to form the mixture generally indicated as 25 in the tank 20. The nutrient feed is typically provided as a continuous flow during the fermentation process. In the tank 20, an agitator 26 is arranged configured to agitate the mixture. In the tank, an air sparger 28 is arranged within the tank 20 for providing air to the mixture. The tank 20 also have a discharge port 30 having a meters 32 and 34 arranged thereon. By way of example, the meter 32 is shown as a Coriolis meter, and the meter 34 is shown as a SONAR meter, for providing measurements of the mixture 25 being provided via the discharge port 30. During the process, a continuous flow of well mixed sample flows through the meters 32, 34, where the SONAR meter 34 is configured to measure the amount of entrained air in the mixture forming part of the fermentation process in the tank 20 and to provide the signal containing information about the amount of entrained air in the mixture.

In operation, by adding a device that can measure the amount of entrained air (gas void fraction) in the effluent or discharge from the tank 20, an indication of the level of foam in the tank 20 can be derived. The amount of foam produced will be directly related to the magnitude of the entrain air (gas void fraction) detected in the tank discharge from the discharge port 30. This information can be used to control the amount of defoamer added to that tank to more precisely control the production of foam within the tank 20 by controlling the amount of defoamer added.

By way of example, one device 34 that can be used to measure the entrain air (gas void fraction) in the discharge is the GVF-100 meter developed by the assignee of the instant patent application.

In alternative embodiments according to the present invention, instead of placing the entrained air measurement device on the discharge port 30, the measurement device may be placed on another location to measure a representative sample of the mixture with in the tank. For example, FIG. 4 shows a fermentation process generally indicated as 218 having a by-pass loop 230 that is set up on the side of the tank 220 to circulate a sample of the mixture through a pipe 230a having the air measurement device installed. In FIG. 4 elements similar to that shown in FIG. 2 are similarly labeled and perform substantially the same function in relation to implementing the present invention. For example, consistent with that described above, the SONAR meter 34 is configured to measure the amount of entrained air in the mixture flowing in by-pass loop 230 and forming part of the fermentation process in the tank 20 and to provide the signal containing information about the amount of entrained air in the mixture.

Alternatively, the mixture may be measured directly by installing a gas void fraction measurement device within the tank, such as a GH-100 developed by the assignee of the instant patent application.

FIG. 3

Figure 3:
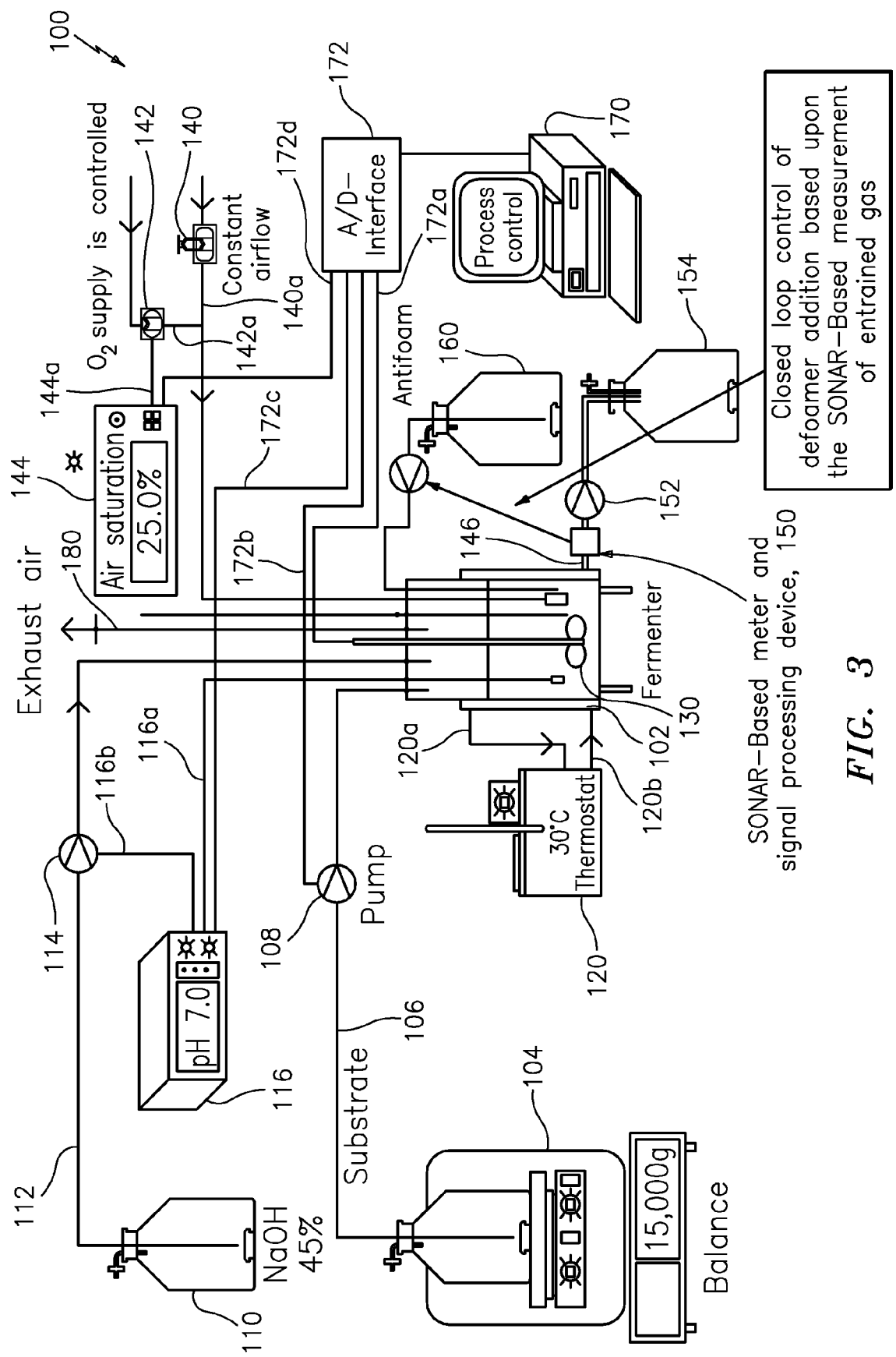
FIG. 3 is a diagram of a system for implementing a fermentation process according to some embodiment of the present invention.

FIG. 3 shows a lysine fermentation process generally indicated as 100 for processing a mixture in a fermenter tank 102 according to some embodiments of the present invention. The fermenter tank 102 is arranged in relation to a tank 104 for providing a substrate along a line 106 via a pump 108 to the fermenter tank 102, and also in relation to a tank 110 for providing NaOH along a line 112 via a pump 114 to the fermenter tank 102. A pH control device 116 is arranged in relation to the pump 114 and the fermenter tank 102 and configured to sense the pH of the mixture along line 116a and control the pump 114 along a control line 116b for providing the NaOH based at least partly on the sensed pH of the mixture. A temperature control device 120 is arranged in relation to the pump 114 and the fermenter tank 102 and configured to control the temperature of the mixture in the fermenter tank 102 by processing a flow to and from the fermenter tank 102 via lines 120a and 120b. An agitator 130 is arranged inside the fermenter tank 102 and configured to agitate the mixture. A device 140 is arranged to provide a constant airflow along line 140a to the fermenter tank 102; a device 142 and an air saturation control device 144 are arranged to provide a supply of oxygen ($O^2$) along a line 142a to the fermenter tank 102 via line 140a; and the air saturation control device 144 controls the device 142 via a control line 144a.

During the fermentation process 100, a continuous flow of well mixed sample flows via a discharge port 146 is pumped through a SONAR-based meter and signal processing device 150 according to the present invention using a pump 152 into a tank 154, where the SONAR-based meter and signal processing device 150 is configured to measure the amount of entrained air in the mixture forming part of the fermentation process in the fermenter tank 102, determine a level of foam in the tank based at least partly on the amount of entrained air in the mixture, and provide a control signal containing information for controlling the amount of defoamer added to the mixture in the fermenter tank 102 so as to control the production of foam within the tank 102 by controlling the amount of defoamer provided from a tank 160 added to the mixture in the fermenter tank 102. As shown, a closed loop control of the deformer addition is based on the SONAR-based measurement of entrained air.

The fermentation process 100 may also include using a process control device 170 and ND interface device 172 for exchanging process control signalling, e.g., with the agitator 130 via line 172a, with the pump 108 via line 172b, with the pH control device 116 via line 172c and with the air saturation control device 144 via line 172d.

As shown, exhaust is provided from the tank 102 via an exhaust line 180.

The Entrained Air Measurement Device 12 and Associated Data Gathering or Sensing Technology The SONAR-based entrained air measurement device 12 and associated data gathering or sensing technology is known in the art, and the scope of the invention is not intended to be limited to any particular type or kind thereof either now known or later developed in the future. By way of example, the associated data gathering or sensing technology may include the GH-100 and/or GVF-100 meter developed by the assignee of the instant patent application. The associated data gathering or sensing technology may include in whole or in part devices disclosed in U.S. Pat. Nos. 7,165,464; 7,134,320; 7,363,800; 7,367,240; and 7,343,820, which are all incorporated by reference in their entirety. The sensing technology disclosed in these cited patents may also be referred to herein as SONAR sensing technology, which was developed be the assignee of the present invention. The scope of the invention is also intended to include using other types or kind of apparatus, device, systems etc. for entrained air measurement either now known or later developed in the future.

FIG. 5

The Signal Processor 14

The apparatus according to some embodiments of the present invention may also take the form of the signal processor 14 itself as shown in FIG. 5. Consistent with that shown in FIG. 1, the signal processor 14 includes one or more other modules 16 configured to receive the signal containing information about the amount of entrained air in the mixture forming part of the fermentation process in the tank, and determine the level of foam in the tank based at least partly on the amount of entrained air in the mixture.

The one or more other modules 16 configured to implement functionality in relation to signal processing may include, but not be limited to, input/output, random access memory, read only memory, busing etc. The functionality of the one or more modules 16 of the signal processor 14 may be implemented using hardware, software, firmware, or a combination thereof. In a typical software implementation, the processor modules would include one or more microprocessor-based architectures having a microprocessor, a random access memory (RAM), a read only memory (ROM), input/output devices and control, data and address buses connecting the same. A person skilled in the art would be able to program such a microprocessor-based implementation to perform the functionality described herein without undue experimentation. The scope of the invention is not intended to be limited to any particular type or kind of signal processing technology either now known or later developed in the future, and embodiments are envisioned using other types or kinds of signal processing technology either now known or later developed in the future.

The one or more modules may also be implemented as apparatus taking the form of a computer-readable storage medium having computer-executable components for performing the steps of the aforementioned method.

The Various Fermentation Processing Device

The fermentation processes described herein includes various processing device, including but not limited to a tank, feed lines, an air sparger, an agitator, pumps, a temperature measurement or control device, etc. which are all known in the art. The scope of the invention is not intended to be limited to any particular type or kind of such various devices either now known or later developed in the future, and embodiments are envisioned using other types or kinds of such various devices either now known or later developed in the future.

Applications

Although the scope of the invention is described in relation to fermentation processes, including for processing lysine, the scope of the invention is intended to include applications or processes where determine a level of foam in a mixture needs to be determined and/or controlled. For example, the applications may include other types or kind of fermentation processes for processing other types or kind of products either now known or later developed in the future, including other types or kind of industrial processes either now known or later developed in the future.

The Scope of the Invention

While the invention has been described with reference to an exemplary embodiment, it will be understood by those skilled in the art that various changes may be made and equivalents may be substituted for elements thereof without departing from the scope of the invention. In addition, modifications may be made to adapt a particular situation or material to the teachings of the invention without departing from the essential scope thereof. Therefore, it is intended that the invention not be limited to the particular embodiment(s) disclosed herein as the best mode contemplated for carrying out this invention.

What is claimed is:

1. A signal processor comprising:
one or more modules configured to:
receive a signal containing information about an amount of entrained air in a mixture forming part of a fermentation process in a tank; and
determine a level of foam in the tank based at least partly on the amount of entrained air in the mixture.

2. A signal processor according to claim 1, wherein the level of foam in the tank is determined based at least partly on the amount of foam produced in the tank being directly related to the magnitude of the entrain air detected in the mixture.

3. A signal processor according to claim 1, wherein the signal processor is configured to receive the signal from an entrained air measurement device configured to measure the amount of entrained air in the sample of mixture and to provide the signal based at least partly on the measurement of the amount of entrained air in the sample of the mixture.

4. A signal processor according to claim 1, wherein the information contained in the signal is based at least partly on the speed of sound propagating through the mixture.

5. A signal processor according to claim 1, wherein the one or more modules is configured to provide a control signal for controlling an amount of defoamer added to the mixture in the tank so as to control the production of foam within the tank by controlling the amount of defoamer added to the mixture in the tank.

6. A signal processor according to claim 1, wherein the signal processor forms part of a fermentation process for fermenting lysine.

7. A signal processor according to claim 1, wherein the one or more modules is configured to provide signalling to control an antifoam device configured to provide an amount of defoamer added to the mixture in the tank so as to control the production of foam within the tank.

8. A signal processor according to claim 1, wherein the signal processor forms part of a closed loop control configured to provide a foamer addition based at least partly upon a measurement of entrained gas.

9. A signal processor according to claim 1, wherein the signal processor is configured to receive the signal from an entrained air measurement device configured to measure a sample of the mixture either as an effluent or discharge provided from the tank via a discharge port, or as a representative sample provided from the tank via a by-pass loop, or by measuring the sample of the mixture directly in the tank.

10. A signal processor according to claim 9, wherein the signal processor is configured to receive the signal from an entrained air measurement device arranged in relation to the discharge port configured to measure the amount of entrained air in the effluent or discharge from the tank and to provide the signal based at least partly on the measurement of the amount of entrained air in the effluent or discharge from the tank.

11. A signal processor according to claim 9, wherein the signal processor is configured to receive the signal from an entrained air measurement device arranged in relation to the by-pass loop configured to measure the amount of entrained air in the representative sample of the mixture within the tank and to provide the signal based at least partly on the measurement of the amount of entrained air in the representative sample of the mixture.

12. A signal processor according to claim 9, wherein the signal processor is configured to receive the signal from a by-pass loop set-up arranged on the side of the tank to circulate the mixture through a pipe having the entrained air measurement device arranged thereon.

13. A signal processor according to claim 9, wherein the signal processor is configured to receive the signal from an entrained air measurement device arranged within the tank configured to measure the amount of entrained air in the mixture within the tank and to provide the signal based at least partly on the measurement of the amount of entrained air in the mixture within the tank.

14. A method comprising:
receiving a signal containing information about an amount of entrained air in a mixture forming part of a fermentation process in a tank; and
determining a level of foam in the tank based at least partly on the amount of entrained air in the mixture.

15. A method according to claim 14, wherein the level of foam in the tank is determined based at least partly on the amount of foam produced in the tank being directly related to the magnitude of the entrain air detected in the mixture.

16. A method according to claim 14, wherein the method comprises measuring a sample of the mixture either as an effluent or discharge provided from the tank via a discharge port, or as a representative sample provided from the tank via a by-pass loop, or by measuring the sample of the mixture directly in the tank.

17. A method according to claim 14, wherein the method comprises fermenting lysine in a fermentation process.

18. A method according to claim 14, wherein the method comprises arranging an antifoam device configured to provide an amount of defoamer added to the mixture in the tank so as to control the production of foam within the tank.

19. A method according to claim 14, wherein the method comprises agitating the mixture in the tank, including using an agitator arranged within the tank; or providing air to the mixture in the tank, including using an air sparger arranged within the tank; or a combination thereof.

20. A method according to claim 14, wherein the method comprises using a closed loop control configured to provide a foamer addition based at least partly upon a measurement of entrained gas.

21. A method according to claim 14, wherein the method comprises arranging an entrained air measurement device configured to measure the amount of entrained air in the mixture and to provide the signal based at least partly on the measurement of the amount of entrained air in the mixture.

22. A method according to claim 21, wherein the information contained in the signal is based at least partly on the speed of sound propagating through the mixture.

23. A method according to claim 21, wherein the method comprises providing a control signal for controlling an amount of defoamer added to the mixture in the tank so as to control the production of foam within the tank by controlling the amount of defoamer added to the mixture in the tank.

24. A method according to claim 21, wherein the method comprises arranging an entrained air measurement device in relation to the discharge port configured to measure the amount of entrained air in the effluent or discharge from the tank and to provide the signal based at least partly on the measurement of the amount of entrained air in the effluent or discharge from the tank.

25. A method according to claim 21, wherein the method comprises arranging an entrained air measurement device within the tank configured to measure the amount of entrained air in the mixture within the tank and to provide the signal based at least partly on the measurement of the amount of entrained air in the mixture within the tank.

26. A method according to claim 21, wherein the method comprises arranging an entrained air measurement device in relation to the by-pass loop configured to measure the amount of entrained air in the representative sample of the mixture within the tank and to provide the signal based at least partly on the measurement of the amount of entrained air in the representative sample of the mixture.

27. A method according to claim 26, wherein the method comprises arranging a by-pass loop set-up on the side of the tank to circulate the mixture through a pipe having the entrained air measurement device arranged thereon.

28. A method according to claim 14, wherein the method comprises providing either a stock feed, a nutrient feed, or some combination thereof.

29. A method according to claim 28, wherein the nutrient feed is provided as a continuous flow during the fermentation process.

30. Apparatus, including a system, comprising:
an entrained air measurement device configured to measure the amount of entrained air in a mixture forming part of a fermentation process in a tank and to provide a signal containing information about an amount of entrained air in the mixture; and
a signal processor having one or more modules configured to receive the signal containing information about the amount of entrained air in the mixture forming part of the fermentation process in the tank, and determine a level of foam in the tank based at least partly on the amount of entrained air in the mixture.

31. Apparatus according to claim 30, wherein the level of foam in the tank is determined based at least partly on the amount of foam produced in the tank being directly related to the magnitude of the entrain air detected in the mixture.

32. Apparatus according to claim 30, wherein the information contained in the signal is based at least partly on the speed of sound propagating through the mixture.

33. Apparatus according to claim 30, wherein the one or more modules is configured to provide a control signal for controlling an amount of defoamer added to the mixture in the tank so as to control the production of foam within the tank by controlling the amount of defoamer added to the mixture in the tank.

34. Apparatus according to claim 30, wherein the system is configured to ferment lysine in a fermentation process.

35. Apparatus according to claim 30, wherein the system comprises an antifoam device configured to provide an amount of defoamer added to the mixture in the tank so as to control the production of foam within the tank.

36. Apparatus according to claim 30, wherein the system comprises an agitator arranged in the tank and configured to agitate the mixture in the tank; or air sparger arranged within the tank configured to provide air to the mixture in the tank; or a combination thereof.

37. Apparatus according to claim 30, wherein the system comprises the signal processor forms part of a closed loop control configured to provide a foamer addition based at least partly upon a measurement of entrained gas.

38. Apparatus according to claim 30, wherein the entrained air measurement device configured is configured to measure a sample of the mixture either as an effluent or discharge provided from the tank via a discharge port, or as a representative sample provided from the tank via a by-pass loop, or by measuring the sample of the mixture directly in the tank.

39. Apparatus according to claim 38, wherein the entrained air measurement device is arranged in relation to the discharge port and configured to measure the amount of entrained air in the effluent or discharge from the tank and to provide the signal based at least partly on the measurement of the amount of entrained air in the effluent or discharge from the tank.

40. Apparatus according to claim 38, wherein the entrained air measurement device is arranged within the tank and configured to measure the amount of entrained air in the mixture within the tank and to provide the signal based at least partly on the measurement of the amount of entrained air in the mixture within the tank.

41. Apparatus according to claim 38, wherein the entrained air measurement device is arranged in relation to a by-pass loop set-up and configured to measure the amount of entrained air in the representative sample of the mixture within the tank and to provide the signal based at least partly on the measurement of the amount of entrained air in the representative sample of the mixture.

42. Apparatus according to claim 41, wherein the by-pass loop set-up is configured on the side of the tank to circulate the mixture through a pipe having the entrained air measurement device arranged thereon.

43. Apparatus according to claim 30, wherein the system comprises one or more devices configured to provide either a stock feed, a nutrient feed, or some combination thereof.

44. Apparatus according to claim 43, wherein the nutrient feed is provided as a continuous flow during the fermentation process.

45. Apparatus, including a computer-readable storage medium, having computer-executable components for implementing a method comprising: receiving a signal containing information about an amount of entrained air in a mixture forming part of a fermentation process in a tank; and determining a level of foam in the tank based at least partly on the amount of entrained air in the mixture, when run on a signal processor running on a computer device.

46. Apparatus comprising:
    means for receiving a signal containing information about an amount of entrained air in a mixture forming part of a fermentation process in a tank; and
    means for determining a level of foam in the tank based at least partly on the amount of entrained air in the mixture.

* * * * *